United States Patent [19]

Peterson

[11] Patent Number: 5,600,075
[45] Date of Patent: Feb. 4, 1997

[54] HIGH PRESSURE GAS SAMPLE COLLECTION SYSTEM

[76] Inventor: Roger Peterson, County Rd., 375, Drawer 567, Old Ocean, Tex. 77463

[21] Appl. No.: 611,002

[22] Filed: Mar. 5, 1996

[51] Int. Cl.$^6$ ........................................... G01N 1/00
[52] U.S. Cl. ........................................... 73/863.71
[58] Field of Search ................... 73/863.71, 863.72, 73/863.86, 864.51, 864.91

[56] References Cited

U.S. PATENT DOCUMENTS 4,628,749 12/1986 Rafter, Jr. .
5,116,330 5/1992 Spencer .................. 73/863.71
5,251,495 10/1993 Kuhner .................. 73/863.71
5,345,828 9/1994 Peterson ................. 73/863.57

*Primary Examiner*—Robert Raevis
*Attorney, Agent, or Firm*—Gunn & Associates, P.C.

[57] ABSTRACT

The present disclosure sets out a sample collection system which involves a single valve having six ports and two positions. The valve is operated to isolate two ports so that the system process flows into the valve. In the other position of the valve, a sample loop is filled. The sample loop includes a sample storage container. The sample loop connects with the container through quick disconnects and separate isolation valves.

15 Claims, 2 Drawing Sheets

HIGH PRESSURE GAS SAMPLE COLLECTION SYSTEM

BACKGROUND OF THE DISCLOSURE

The present disclosure is directed to a high pressure gas collection system and more particularly to a system which collects samples to be taken to a laboratory so that the gas samples can be tested and an assay provided. It is especially important to do this in the buying and selling of expensive gaseous products which are manufactured in great volumes by very large petrochemical plants. More particularly, the system collects a sample without permitted out-gassing or other bleeding to atmosphere or loss of components in the course of collection and transfer. Typically, a gas sample is a mix of several different gases which may have different vapor pressures where some may leak more or less readily through seals to atmosphere. U.S. Pat. No. 5,345,828 of the present inventor sets forth a process plant sample collection system. In that, a process is trapped so that a sample can be obtained. The sample is delivered through a buffer tank 42 and is ultimately accumulated in a sample container 20. The sample container is isolated with a septa across the narrow neck of the container. While this system has met with significant success, it is limited in that it is best used for liquids which are dropped to a pressure near atmospheric pressure. Moreover, it operates in a system which includes a nitrogen purge gas. This helps assure that the system is kept clear. The nitrogen purge step is avoided by the high pressure gas delivery system of this disclosure.

More recently, U.S. Pat. No. 5,396,812 issued and shows certain elements of the same structure. Again, it is a successful system which particularly finds use and application in handling of materials which are brought near to atmospheric pressure. It is particularly important to note that is has a closed system where the sample is isolated with nitrogen input to the sample collection system. Notwithstanding the incorporation of the nitrogen gas isolation, the system works quite well to provide isolated samples, and the isolated samples are received in the appropriate storage container. This storage container can maintain a modest level of pressure on the interior.

Both of the foregoing sample systems are quite successful. Moreover, both are particularly effective for collecting samples where the fluid in the system is not highly pressured and where the sample is liquid. The present disclosure is directed to an entirely different system. It is particularly useful for a sample source where the material in question typically is provided at elevated pressure or elevated temperature or both. While there is a superficial structural similarity between the prior systems and this disclosure in the implementation of a two position, six port valve, the handling of the sample is significantly different. This system is especially useful for fluids which are substantially in the vapor phase. In the vapor phase, sample capture and delivery into a container is more difficult. In the vapor phase, there is the possibility of the gas seeping through a perforated septa or other seal membrane closing a container. In the present disclosure, the sample can be provided at an elevated or highly elevated pressure, temperature or both and can be captured in a container without vapor loss so that it can be taken to a laboratory for testing.

The present disclosure sets forth a six port, two-way valve which enables a sample to be removed from a flowing process such as a petrochemical plant and in particular part of the plant where the flowing fluids are at extremely high pressures or temperatures, and often at both high pressure and temperature. Through the use of the present disclosure, an individual closed sample chamber is installed in the system. It is first opened within the system and any gases which may be residual in the container are purged through the system to atmosphere preferably by bleeding off to atmospheric pressure through a check valve which connects with an optional flare. Bleeding through the flare assures that the discharge is appropriately combusted for safety. The system also incorporates a sample cylinder having two ports with isolation valves at the two ends of the sample cylinder. The two ports also connect with isolation valves and then connect there beyond to quick disconnect fittings. The quick disconnect fittings enable the disconnection of the sample cylinder after it has been filled to high pressure. The isolation valves enable isolation of the system from the sample container so the sample is not diluted or otherwise mixed with unintended gases from atmosphere. The container connected isolation valves and quick release fittings also enable the isolation of the sample container so that the sample container can be carried in a truck or other vehicle. Even though the sample cools within the sample container, and the pressure drops accordingly, the sample remains isolated for delivery to the testing facility. By using multiple sample containers (tagged and labeled with sample date and time), sample portability enables testing notwithstanding the high pressure in the product system. The present disclosure has the advantage that it is a relatively simple system and yet it is particularly able to operate to fill sample containers in scheduled order.

Directing attention now to the present disclosure, it sets forth both an apparatus and method for use of the apparatus with a view of obtaining a sample. The sample is provided from a process which is connected to the present apparatus through a two-position, six-port valve. By appropriate routing, a sample container is filled. The sample container is provided with two ends so that fluid flows fully through it. The container has two ends connected with isolation valves. The valves assure container portability without leakage. Dismounting is done by two quick release connections.

In summary, the present disclosure sets forth a six-port, two-way valve having a single valve structure. This enables switching of the sample container into and out of a connected control valve so that processed fluid can be delivered into and out of the sample container. The sample container is preferably provided with two fittings. The sample container is an elongate cylinder having fittings at opposite ends, and the two opposite ends are each provided with isolation valves and quick disconnect fittings. This defines a portable structure which can be carried to another location for testing. This enables the contents of the sample container to be isolated without leakage so that the material can be tested at a testing laboratory.

IN THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may add to other equally effective embodiments.

FIG. 1 of the drawings shows the sample filling apparatus of the present disclosure and illustrates a flow path for the sample container through the valve system;

DETAILED DESCRIPTION OF THE PREFERRED EMBODIMENT

Figure 1:
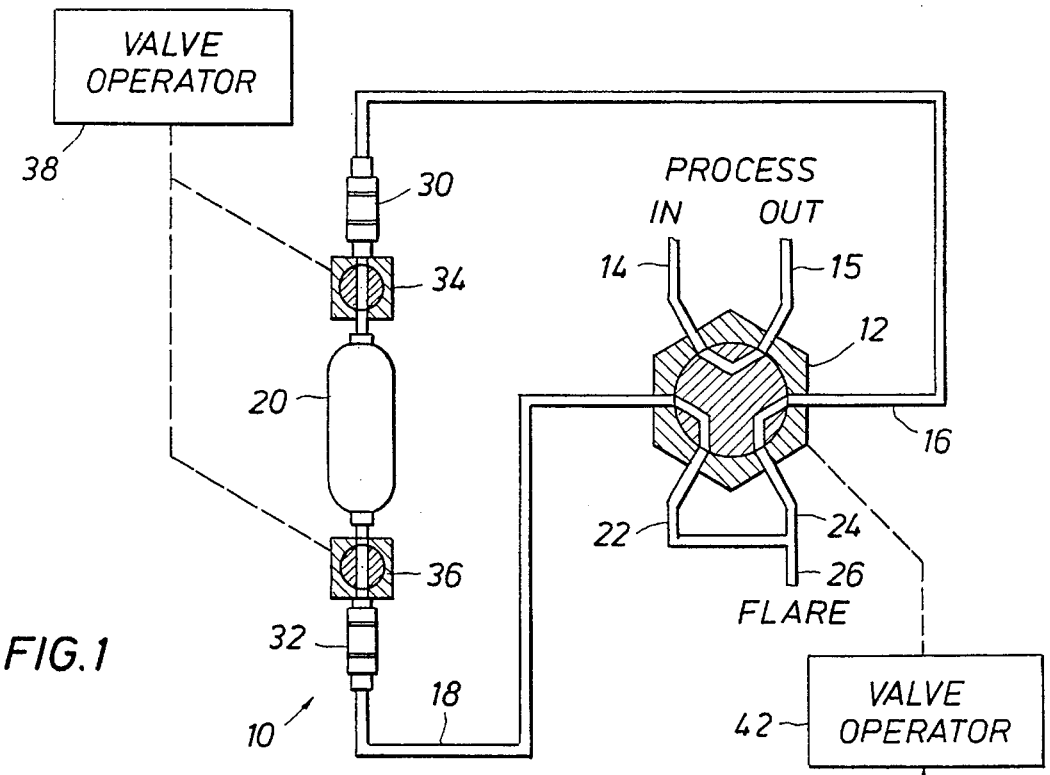

Attention is now directed to FIG. 1 of the drawings which shows the present invention. It is indicated generally by the numeral 10 which will be described as a high pressure sample collection system. A method of operation will also be set forth. A valve 12 provides control of fluid flow. The valve 12 is preferably a six-port, two-position valve which has one inlet port connected to a line 14 communicating with a process, and a process return line 15 connects with a second port or outlet port. These two ports make up the connections to the process which will be discussed in some detail below. Another port of the valve 12 is connected with a sample loop 16. The sample loop enables filling of a sample container 20. The sample loop continues with the line 18 which connects to a fourth port. In addition, the valve 12 includes two ports, namely, the ports 22 and 24 which connect from the valve 12 to a check valve 26 which then communicates with a flare. This assures safe disposal of any lost fluid.

FIG. 1 additionally shows certain important aspects of the sample container 20. Duplicate quick disconnect fittings 30 and 32 are incorporated. The two disconnects 30 and 32 connect serially with isolation valves 34 and 36. In the preferred form, the valves 34 and 36 are quarter turn valves which completely block flow. A valve handle has been included in the view to show in a symbolic form that the valves are open. Thus, they are open in FIG. 1 and closed in FIG. 3 as evidenced by the different handle positions reflected in the two views. The valves 34 and 36 are powered by a valve operator 38. The valve operator is subject to control of a timer 40 which is connected to it. In like fashion, the timer 40 is connected to another valve operator 42 which then connects with the valve 12 to operate it between the two positions necessary for system operation.

To provide a context for the practice of the present invention, assume that the process is a chemical manufacturing process where a gaseous fluid at very high pressure and high temperature is being manufactured. Whether the final product or an intermediate is tapped, the lines 14 and 15 connect with the process to obtain the requisite sample flow in an endless loop through the lines 14 and 15. This brings sample to the system 10 so that the product can be tested. The process itself may involve flow in a very large conduit or pipe. It is not necessary to have a large flow for the sample collection system 10 of this disclosure. Indeed, the lines 14 and 15 providing the connections can be relatively small, perhaps one-quarter inch or even smaller. The purpose of this present system is to obtain an accurate sample, not necessarily a large sample. For that reason, relatively small lines, including lines as small as one-eighth inch can be used. The valve 12 is a valve provided by Valco Manufacturing Company. It is a relatively small valve which can handle and switch pressures of several thousand psi without leaking. The sample lines are connected with the valve 12 through the use of suitable fittings which assure leak free connection.

Once the connections are made to the system 10, sample flows through the loop which is defined through the ports 14 and 15. That loop is isolated as shown in FIG. 1 of the drawings. That is, there is no flow except in that loop. By contrast, the sample loop which connects through the container 20 is maintained at a minimal pressure. It is preferably open so that any residue in that loop can be voided to the exterior and that is delivered through the flare. The check valve 26 assures that atmosphere gas does not leak back into this loop.

Figure 2:
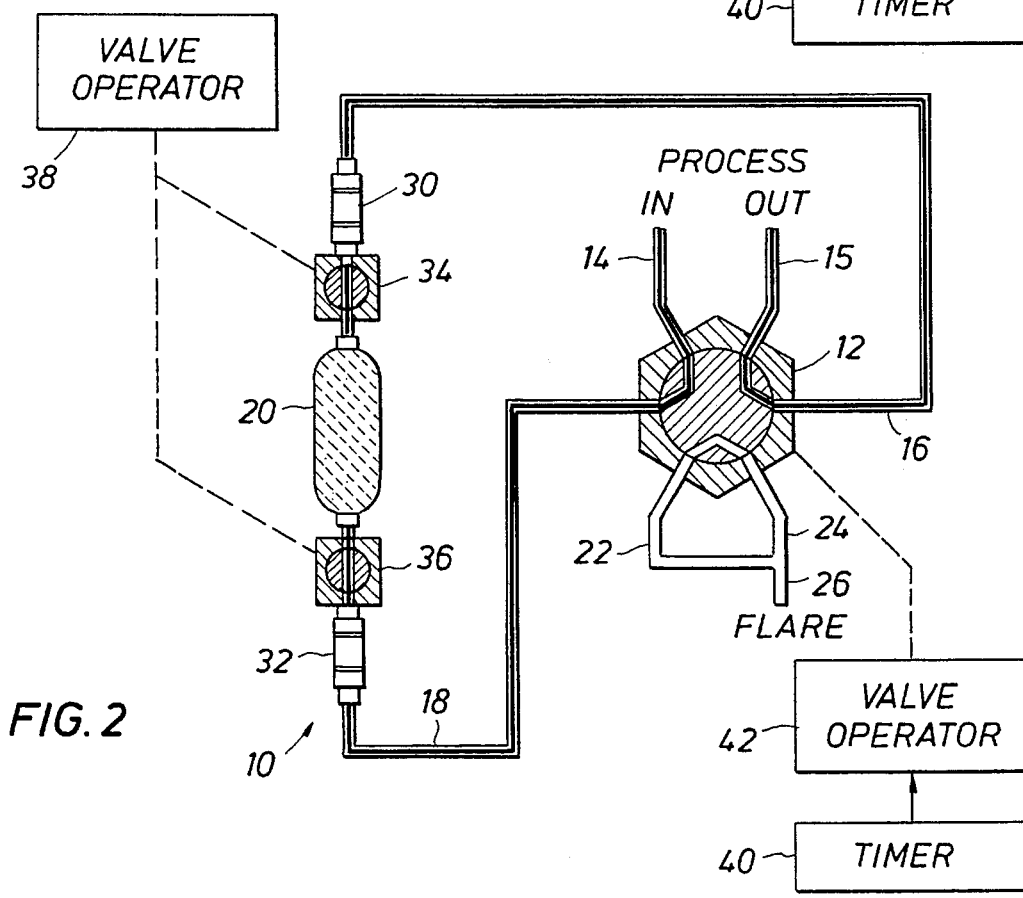
FIG. 2 is a view of the same system as shown in FIG. 1 showing an altered set of connections by operation of the valve so that process pressure is delivered and flows through the sample container.

FIG. 2 shows operation of the system 10 after the valve 12 has been switched. Flow is directed from the port 14 and the connected line. This delivers flow in to the sample container 20. As previous noted, the isolation valves 34 and 36 must be open to accomplish this. When flow is input to the container 20, the valves are left in that condition for at least a few seconds, and preferably for a few minutes. As the flow continues endlessly, the sample container 20 captures continuously a refreshed and replaced measure of process gas. This is illustrated in FIG. 2 where flow continues without interruption. Typically, it will be necessary to connect the process lines 14 and 15 at selected locations of the process to obtain some pressure differential to assure that there will be a fluid pressure drive for the system 10. Even a differential of two or three psi is adequate to continue the flow.

Figure 3:
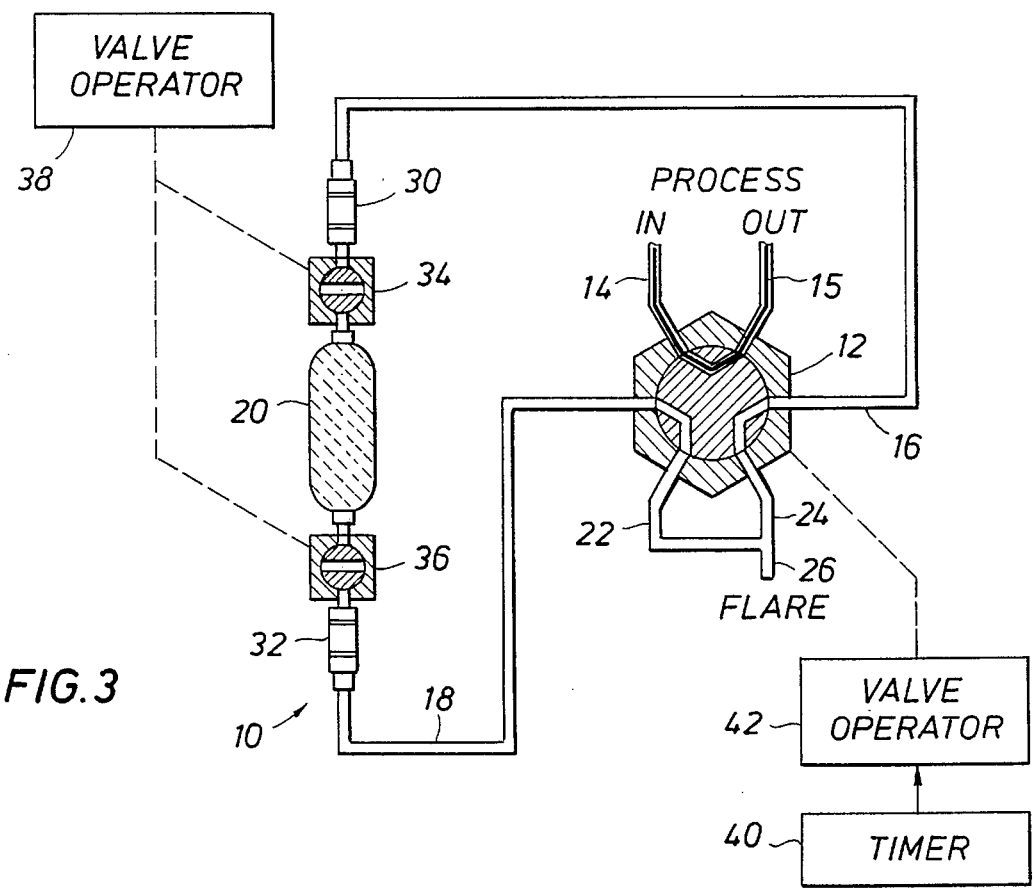
FIG. 3 is a view similar to FIG. 1 showing the sample container isolated by closing the valves connected to it.
Figure 4:
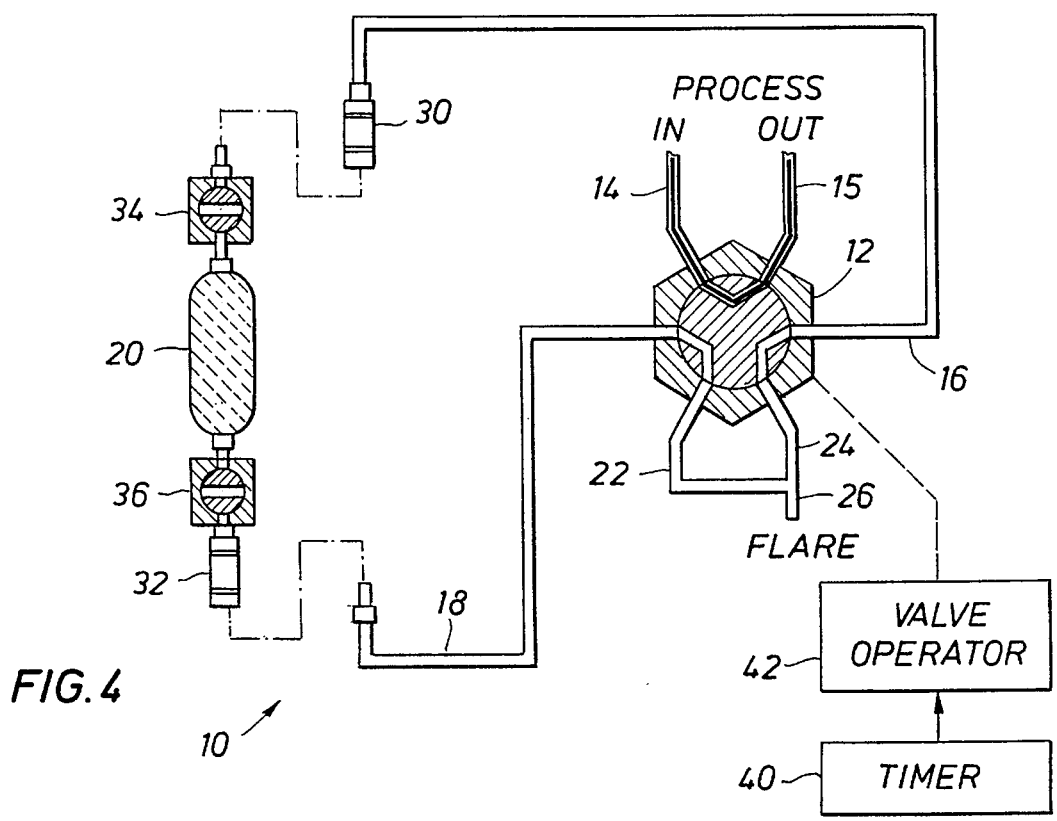
FIG. 4 is a view similar to FIG. 3 showing the isolated sample container disconnected for transportation elsewhere and to enable replacement with another sample container.

Going now to FIG. 3 of the drawings, it shows the equipment deployed in the same operative conditions as shown in FIG. 2 except the valves 34, 36 and 12 have been operated. Valve closure blocks flow through the sample loop. This also assures that measured portion from the sample loop is captured in the sample container 20. This is accomplished by switching the blocking valves 34 and 36. They are switched preferably simultaneously. This also assures that the two valves on switching simultaneously maintain the pressure in the container 20 at the elevated pressure. Assume for an example that pressure in the process is 1,000 psi. If so, the pressure in the sample container 20 is very close to 1,000 psi. The valves 34 and 36 are closed to capture the sample at this high pressure. While there may be some cooling subsequent to closure and some loss of pressure as a result of cooling and condensation, the sample remains intact within the container. Capture of the sample in this fashion assures the sample does not escape and does not boil off thereby losing more volatile components in the sample. FIG. 3 also shows the operation of the valve 12 back to the position shown in FIG. 1 of the drawings. The sample container is disconnected from the process as shown in FIG. 4. It is wise to do this so that there is no risk of leakage through the disconnects 30 and 32.

To summarize, the difference between FIG. 2 and FIG. 3 involves the operation of the valves 34, 36 and 12. To proceed from the posture of FIG. 2, the blocking valves 34 and 36 are first closed and then the valve 12 is operated. The difference between FIG. 3 and FIG. 4 involves operation of the disconnects 30 and 32. They are operated to remove the sample container and install it in a test laboratory. They also involve the break in the sample loop to remove the sample container so that a duplicate sample container can be plugged into the quick disconnects. If needed, the sample containers can be replicated in any number desired to obtain samples. If the distance from the test equipment 10 to the test laboratory is not great, only two are needed so that one is installed and the other is transported to the laboratory. In another aspect, however, it may be necessary to provide several sample containers so that a daily sample can be obtained and only one trip made for the week. In that instance, it may require a minimum of eight sample containers so that seven for the week can be taken to a test laboratory. Again, this depends on the distance to the test laboratory and the ease of transportation. As a generalization, the sample containers are preferably all the same size. Typical sizes are acceptable at 1, 2, or 5 liters. Smaller sample containers can be used; however, it is desirable to obtain samples of the size just mentioned.

Because the system is designed to operate at high pressure and high temperature, the sample container is preferably a clad stainless steel structural vessel which is relatively strong and able to resist the internal pressure just mentioned. Moreover, the sample container is preferably constructed with end fittings to enable connection permanently of the isolation valves 34 and 36 and attachment of the quick disconnects.

One aspect of the present system is the impact of the connection to the check valve 26 to the flare. When the system is pressurized as exemplified in FIG. 2 of the drawings, there will be some surplus material in the sample loop which is expelled. It is delivered to the flare for safe discharge. This provides a flow which is always from the equipment to the exterior. This prevents drawing air into the system. After the sample loop has been placed on line as exemplified in FIG. 2 of the drawings, there will certainly be no oxygen left in the system 10. This also is an effective and safe system so that the risk of combustion in the system or an undesired chemical reaction with the hot sample contacting oxygen in the air is markedly reduced.

The system 10 is preferably operated with the timer 40 controlling the operation. Indeed, the timer can be provided with a twenty-four hour clock so that the sample is taken at the same time during the operation of the processing plant. Periodic sampling capability is therefore highly desirable. Periodic sampling is also desirable from the point of view of providing a consistent data pattern in the analysis of samples for process adjustment and control.

One reason for taking the sample is to enable fine tuning of the system process. That often requires a data baseline. The data baseline is established by continual monitoring of the samples and recording the sample data. Whether the samples are taken hourly, daily or less often, the data baseline can be established through the use of the sample collection system 10.

To summarize, a method of operation is also set forth. The method of operation involves the operative steps which are shown in the four views taking into account the operative positions of the valve 12. The isolation valves 34 and 36 are also controlled in the timely fashion. Finally, the operation of the system proceeds through the key steps described above. Last of all, the operation of the system is intended for recycling so that the equipment proceeds in the operative cycle from FIG. 1 through FIG. 4 and repeats that in controlled and timed fashion.

While the foregoing is directed to the preferred embodiment, the scope is determined by the claims which follow.

I claim:
1. A sample collection system for obtaining a pressurized fluid sample from a process, a sample collection system comprising:
   (a) valve means for controlling delivery of the sample from the process, comprising a six port and two position valve which is operated by an operating means;
   (b) flow lines connected to deliver to and from said valve means a sample from the process;
   (c) a sample loop comprising an entry end and an exit end connected to said valve means;
   (d) a demountable sample receiving container for receiving sample at essentially the same pressure as said process;
   (e) entry and exit valves associated with said container which connect into and release from said sample loop to enable said container to be connected in said sample loop, and wherein said sample container along with said valves are removed as a unit to capture process sample at an elevated pressure, and wherein the operation of said valve means by said operating means between a flow position and a no flow position simultaneously terminates sample flow at said entry end and said exit end of said sample loop.

2. The system of claim 1 wherein the entry and exit valves to the sample container are quarter turn valves which allow the sample container to be sealed or unsealed by operating the valves one quarter turn.

3. The apparatus of claim 1 wherein said operating means comprises a timed valve operator for periodic operation connected with said valve means to operate a valve rotor.

4. The system of claim 1 which also comprises a pressure relief valve which allows fluid sample to escape from the system and wherein said valve does not allow fluid to enter the system.

5. The system of claim 4 wherein conduits suitable for high pressure, high temperature fluids are connected to the pressure release valve.

6. The system of claim 4 wherein said pressure release valve connects to a flare.

7. The system of claim 6 comprised also by said flare which burns material exiting said pressure release valve.

8. The system of claim 1 wherein said valve means can be switched between flow and no flow positions, where,
   when in the flow position, fluid will flow from the process, and into an inlet port of said valve means, and past the said valve means, and through said entry end of said sample loop, and through the sample container and through said exit end of said sample loop, and past said valve means, and through an outlet port of said valve means, and back to the process, and where,
   when in the no flow position, conduits between said inlet port of said valve means and said outlet port of said valve means form a closed path for the fluid which does not pass through said sample container.

9. A sample collection system for obtaining a high pressure fluid sample from a process wherein the sample system comprises:
   (a) a two position, multiple port valve means controlling delivery of the sample;
   (b) a removable sample receiving container suitable to receive and store high-pressure, high-temperature fluids;

(c) first and second conduits which are connected to flow high-temperature, high-pressure fluids into and out of said sample container;

(d) first and second conduit valves to control fluid sample flow in the conduits;

(e) wherein said sample container has two openings and one is an entry point and the other is an exit point so fluid sample can pass through the sample container;

(f) first and second conduit disconnects in said first and second conduits to enable said container and said first and second conduit valves to be removed as a unit; and (g) said first and second conduits connect with ports of said valve means to enable said process fluid sample to flow into said sample container while said first and second valves are open, and which trap a fluid sample therein at high pressure on simultaneously closing said first and second valves by a valve operator means.

10. The system of claim 9 wherein said first and second valves comprise serially connected valves switched between flow and no flow positions for the flow of the sample.

11. The apparatus of claim 10 wherein said first and second valves include a handle exposed for operation by said valve operator or alternately for operation by hand.

12. The system of claim 9 wherein said first and second conduits are suitable for high-pressure, high temperature fluids and are connected from said valve means.

13. The system of claim 9 wherein said conduits and sample container comprise a closed sample fluid flow loop connected to said process.

14. The system of claim 13 wherein said loop is pressure relieved through a check valve and a flare.

15. The system of claim 9 also comprising an exit flare and a serially connected check valve which is serially connected between said valve means and a flare.

* * * * *